United States Patent
Lentz et al.

(10) Patent No.: US 6,926,711 B2
(45) Date of Patent: Aug. 9, 2005

(54) ARTICULATING CATHETER FOR CRYOABLATION WITH REDUCED DIAMETER SECTION

(75) Inventors: David J. Lentz, La Jolla, CA (US); Steven W. Kovalcheck, San Diego, CA (US)

(73) Assignee: CryoCor, Inc., San Diego, CA (US)

( * ) Notice: Subject to any disclaimer, the term of this patent is extended or adjusted under 35 U.S.C. 154(b) by 207 days.

(21) Appl. No.: 10/631,024

(22) Filed: Jul. 30, 2003

(65) Prior Publication Data

US 2005/0027334 A1 Feb. 3, 2005

(51) Int. Cl.$^7$ ............................................. A61B 18/18
(52) U.S. Cl. ..................................... 606/21; 604/95.04
(58) Field of Search ............................. 606/21–26, 41; 604/95.04, 95.05; 600/585

(56) References Cited

U.S. PATENT DOCUMENTS

| | | |
|---|---|---|
| 1,060,665 A | 5/1913 | Bell |
| 3,605,725 A | 9/1971 | Bentov |
| 4,245,624 A | 1/1981 | Komiya |
| 4,456,017 A | 6/1984 | Miles |
| 4,586,923 A | 5/1986 | Gould et al. |
| 4,813,434 A | 3/1989 | Buchbinder et al. |
| 4,815,478 A | 3/1989 | Buchbinder et al. |
| 4,886,067 A | 12/1989 | Palermo |
| 4,960,134 A | 10/1990 | Webster, Jr. |
| 4,960,411 A | 10/1990 | Buchbinder |
| 4,976,684 A * | 12/1990 | Broadnax, Jr. ............... 604/540 |
| 4,976,688 A | 12/1990 | Rosenblum |
| 5,037,391 A | 8/1991 | Hammerslag et al. |
| 5,042,985 A | 8/1991 | Elliott et al. |
| 5,108,368 A | 4/1992 | Hammerslag et al. |
| 5,114,414 A | 5/1992 | Buchbinder |
| 5,125,895 A | 6/1992 | Buchbinder et al. |
| 5,190,050 A | 3/1993 | Nitzsche |
| 5,242,441 A * | 9/1993 | Avitall ......................... 606/41 |
| 5,246,430 A * | 9/1993 | MacFarlane ................ 604/524 |
| 5,281,213 A * | 1/1994 | Milder et al. ................. 606/15 |
| 5,318,525 A | 6/1994 | West et al. |
| 5,322,064 A | 6/1994 | Lundquist |
| 5,322,508 A | 6/1994 | Viera |
| 5,330,466 A | 7/1994 | Imran |
| 5,334,145 A | 8/1994 | Lunsquist et al. |
| 5,368,564 A | 11/1994 | Savage |
| 5,507,725 A | 4/1996 | Savage et al. |
| 5,656,030 A | 8/1997 | Hunjan et al. |
| 5,715,817 A | 2/1998 | Stevens-Wright et al. |
| 5,855,560 A | 1/1999 | Idaomi et al. |
| 5,868,735 A * | 2/1999 | Lafontaine ................... 606/21 |
| 5,906,590 A | 5/1999 | Hunjan et al. |
| 5,928,191 A | 7/1999 | Houser et al. |
| 5,944,689 A | 8/1999 | Houser et al. |
| 6,013,052 A | 1/2000 | Durman et al. |
| 6,035,657 A | 3/2000 | Dobak, III et al. |
| 6,066,125 A | 5/2000 | Webster, Jr. |
| 6,106,518 A | 8/2000 | Wittenberger et al. |
| 6,123,699 A | 9/2000 | Webster, Jr. |
| 6,171,277 B1 | 1/2001 | Ponzi |
| 6,183,435 B1 | 2/2001 | Bumbalough et al. |

(Continued)

Primary Examiner—Michael Peffley
(74) Attorney, Agent, or Firm—Nydegger & Associates

(57) ABSTRACT

A catheter usable for cryogenic ablation of tissues is described. The catheter has a deflectable segment with a reduced diameter and a tip portion with a diameter greater than the reduced diameter. A resilient element allows for bending of the deflectable segment preferentially in one plane, and an actuator is used to control the bending of the deflectable segment.

26 Claims, 4 Drawing Sheets

U.S. PATENT DOCUMENTS

| | | |
|---|---|---|
| 6,183,463 B1 | 2/2001 | Webster, Jr. |
| 6,198,974 B1 | 3/2001 | Webster, Jr. |
| 6,210,407 B1 | 4/2001 | Webster |
| 6,254,568 B1 | 7/2001 | Ponzi |
| 6,267,746 B1 | 7/2001 | Bumbalough |
| 6,319,248 B1 | 11/2001 | Nahon |
| 6,332,880 B1 | 12/2001 | Yang et al. |
| 6,346,099 B1 | 2/2002 | Altman |
| 6,413,234 B1 | 7/2002 | Thompson et al. |
| 6,440,126 B1 | 8/2002 | Abboud et al. |
| 6,468,260 B1 | 10/2002 | Bumbalough et al. |
| 6,485,455 B1 | 11/2002 | Thompson et al. |
| 6,500,167 B1 | 12/2002 | Webster, Jr. |
| 6,522,933 B2 | 2/2003 | Nguyen |
| 6,524,296 B1 * | 2/2003 | Beals .......................... 604/500 |
| 6,540,725 B1 | 4/2003 | Ponzi |
| 6,551,271 B2 | 4/2003 | Nguyen |
| 6,569,114 B2 | 5/2003 | Ponzi et al. |
| 6,571,131 B1 | 5/2003 | Nguyen |
| 6,579,278 B1 | 6/2003 | Bencini |
| 6,585,717 B1 | 7/2003 | Wittenberger et al. |
| 6,585,718 B2 | 7/2003 | Hayzelden et al. |
| 6,602,278 B1 | 8/2003 | Thompson et al. |
| 6,605,086 B2 | 8/2003 | Hayzelden et al. |
| 6,607,505 B1 | 8/2003 | Thompson et al. |
| 6,610,058 B2 | 8/2003 | Flores |
| 2001/0025075 A1 | 9/2001 | Smith et al. |
| 2002/0025998 A1 | 2/2002 | McCullough et al. |
| 2002/0062122 A1 | 5/2002 | Lehmann et al. |

* cited by examiner

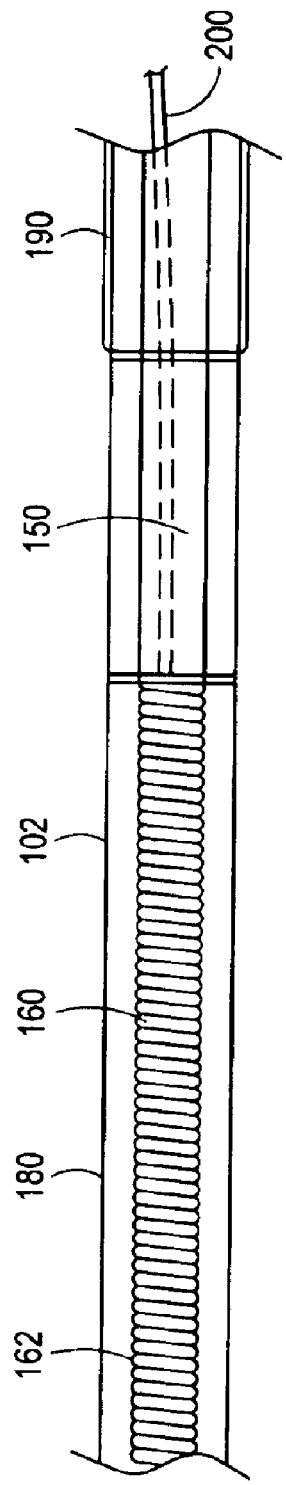
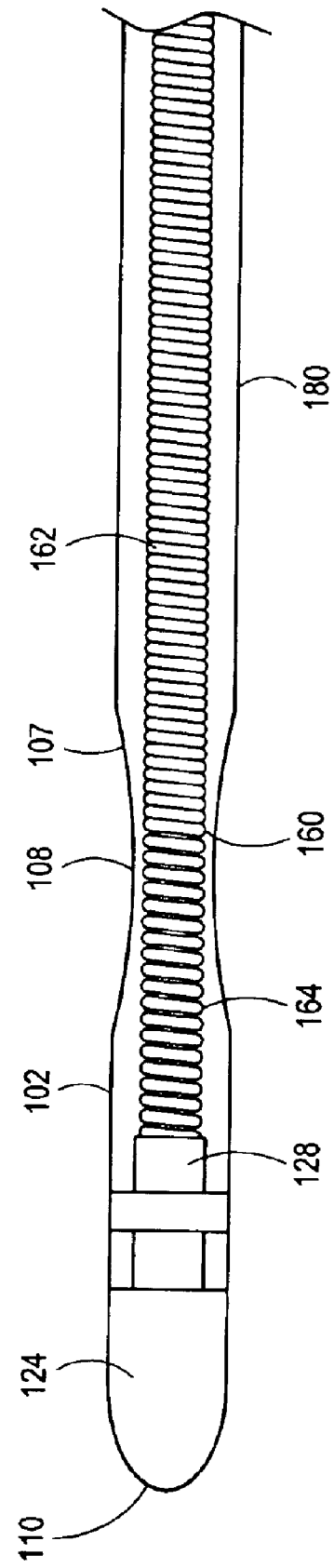
Fig. 4
Fig. 3

ARTICULATING CATHETER FOR CRYOABLATION WITH REDUCED DIAMETER SECTION

FIELD OF THE INVENTION

The present invention relates to cryosurgical catheters, and in particular to cryosurgical catheters articulated for bending.

BACKGROUND OF THE INVENTION

In the treatment of various medical conditions, it is sometimes beneficial to apply an extremely cold temperature at one or more selected, isolated locations in or near an organ in the patient's body. As an example, it can be beneficial in the treatment of cardiac arrhythmia to apply cryosurgical temperatures at selected locations in the patient's heart, to create localized areas of necrotic tissue. Similarly, it can be beneficial to apply extremely cold temperatures at selected locations in other organs, or in a vascular system of the patient. The application of extremely cold temperatures can be achieved by inserting a flexible cryosurgical catheter through a vascular system to the desired location. The flexible catheter can have a heat transfer element at or near its distal end. The heat transfer element can be cooled to a cryosurgical temperature and placed in contact with a selected area of biological tissue.

The application of cold temperatures can be further enhanced by an apparatus with the ability to flex the tip of the cryosurgical catheter in a desired direction, to assist in guiding the catheter through a tortuous path to the selected location in or near a selected organ, or in a vascular system. Tissue targets within the body may be reached more easily if the catheter is made more flexible, and if the tip can deflect over a greater angle.

In light of the above, it is an object of the present invention to provide a cryocatheter with a deflectable tip having sufficient flexibility to precisely position the tip within the vasculature of a patient in accordance with the procedural requirements of a selected surgical application. Another object of the present invention is to provide a cryocatheter with a deflectable tip that is relatively easy to manufacture, is simple to use and is comparatively cost effective.

SUMMARY OF THE INVENTION

According to embodiments of the invention, a surgical device is provided for applying cold temperatures at locations within the human body, via minimally invasive techniques. More specifically, the device may comprise a deflectable catheter, passable through the larger blood vessels and cavities of the heart, having a distal tip which can be deflected by remotely located means. A portion of the catheter near the distal tip is necked down, such that it has a smaller outside diameter than the rest of the catheter. Bending of the catheter takes place at the portion with the smaller diameter, so that the bending radius of the catheter is reduced.

Embodiments of the present invention include a cryogenically cooled apparatus for ablating tissue of a patient. The apparatus includes a handle portion, an elongated catheter extending distally from the handle, the elongated catheter being adapted to transmit a torque imparted by the handle, and a main shaft portion of the catheter having a substantially uniform diameter. The apparatus also includes a deflectable segment at the distal end of the main shaft, the deflectable segment having a minimum diameter that is smaller than the diameter of the main shaft, a tip portion disposed distally of the deflectable segment having a diameter greater than the minimum diameter, the tip portion defining an expansion chamber for refrigerant fluid and having a heat transfer surface in contact with the expansion chamber, a resilient component adapted to define a preferred plane of deflection of the deflectable segment, and an actuator connected to a distal portion of the elongated catheter, adapted to impart a curvature to the deflectable segment.

In another embodiment, the invention is a catheter for surgical applications having a deflectable tip, the catheter including a main shaft portion having a substantially uniform diameter, a deflectable segment of the catheter, the deflectable segment having a minimum diameter that is smaller than the diameter of the main shaft, a tip portion of the catheter disposed distally from the deflectable segment, a resilient component adapted to define a preferred plane of deflection of the deflectable segment, and an actuator linked to the tip portion of the elongated catheter, adapted to impart a curvature to the deflectable segment.

In greater detail, according to the present invention, a cryocatheter has a deflectable tip that can be deflected in a plane through an angle that is substantially equal to 180°. Structurally, the distal aspect of the cryocatheter includes a main shaft portion having a substantially constant first diameter ($d_1$), a tip portion having a substantially same first diameter ($d_1$), and a deflectable segment that interconnects the main shaft portion with the tip portion. A mid point in the deflectable segment that is midway between the tip portion and the main shaft portion, has a second diameter ($d_2$) that is less than said first diameter ($d_1 > d_2$). Also, as indicated above, a resilient component is mounted in the deflectable segment that is shaped and adapted to define a preferred plane of deflection for the deflectable segment.

Deflection of the catheter's tip portion is accomplished during the operation of the cryocatheter by an actuator. More specifically, the actuator is mounted on the handle and is connected through the main shaft to the tip portion. As envisioned for the present invention, manipulation of the actuator will cause the tip portion to move through a range of about 180°. This movement will be in the preferred plan of deflection, and will move the tip portion between a first configuration wherein the tip portion is substantially coaxial with the main shaft portion, and a second configuration wherein it is substantially parallel with the main shaft portion.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is a cross sectional view showing internal structures of a distal tip portion of the catheter according to an embodiment of the present invention;

FIG. 4 is a cross sectional view showing internal structures of a proximal tip portion of the catheter according to an embodiment of the present invention;

DESCRIPTION OF THE PREFERRED EMBODIMENTS

Figure 1:
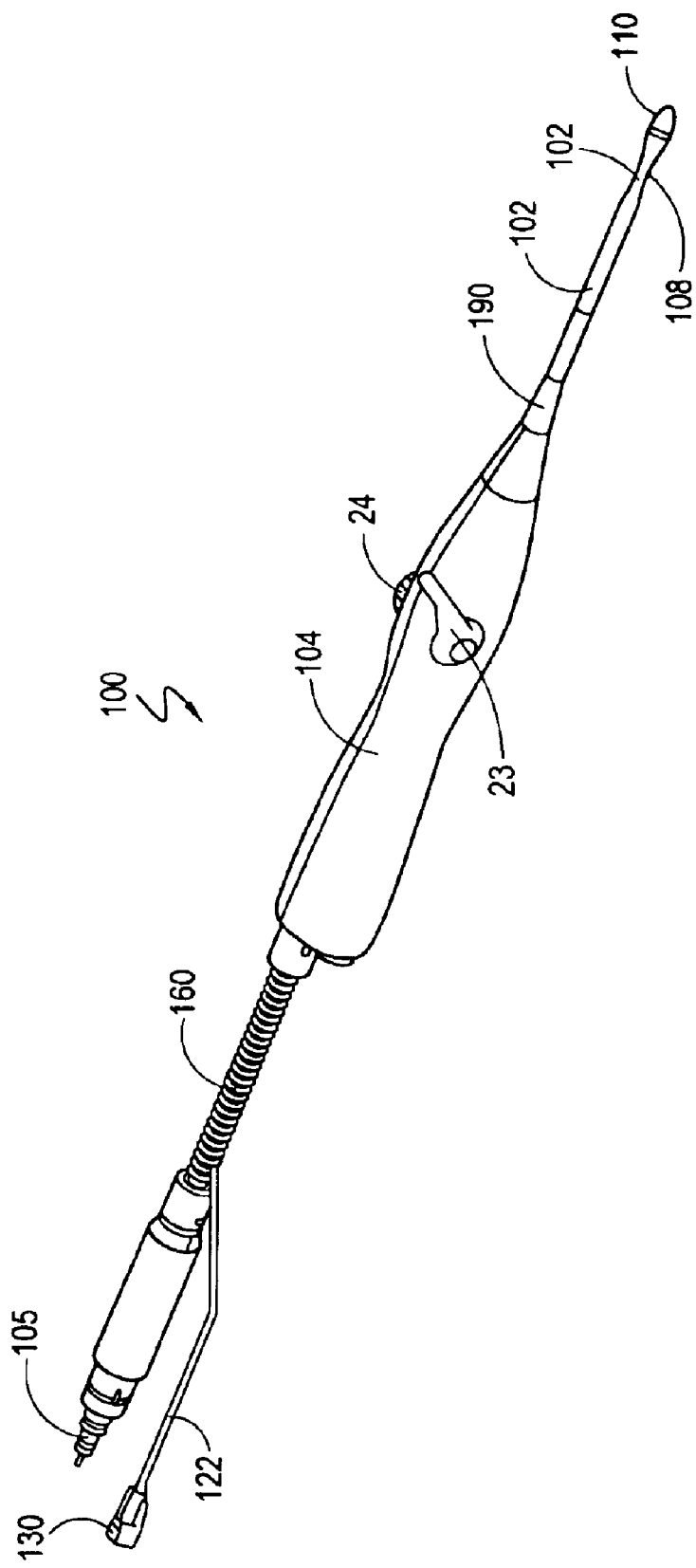
FIG. 1 is a perspective view showing an embodiment of the cryoablation catheter according to the present invention.

The present invention may be further understood with reference to the following description and the appended drawings, wherein like elements are referred to with the same reference numerals.

The cryoablation system according to exemplary embodiments of the present invention has a minimally invasive catheter having a deflectable tip. A remotely bendable section adjacent to the tip allows the tip to move between a neutral, substantially straight position (first configuration), and an angularly displaced position (second configuration). The remotely bendable section has a necked down portion, where the diameter of the catheter is smaller than the diameter at the tip and at portions proximate from the bendable section. Both configurations of the reduced diameter portion allow the catheter to achieve a smaller bending radius than is possible if the diameter is larger. The configurations, as will be explained in greater detail below, maintain a sufficient inner diameter of the catheter such that there is little effect on the pressure of the refrigerant within the catheter.

In one exemplary embodiment according to the present invention shown in FIG. 1, the cryoablation device 100 is designed to apply extremely low temperatures to remote locations within the human body via minimally invasive techniques. More specifically, the deflectable catheter 102 of device 100 may be introduced into the human heart through the larger blood vessels and cavities leading to the heart. The catheter 102 has a distal tip 110 that can be deflected by operating remotely located controls, preferably outside the patient, at a proximal end of the device 100. For example, actuating lever 23 may be manipulated by an operator to deflect tip 110. The catheter 102 includes a reduced diameter section 108 that forms part of a tubular deflectable segment 107 of catheter 102. Catheter 102 may also include internal flexible, multi-conduit vessels that carry a refrigerant fluid from a cryogenic unit (not shown in the drawings) that supplies the pressurized refrigerant to a tip 110 of the catheter 102. A quick disconnect coupling 105 may be used to connect to the cryogenic unit.

As will be described in detail below, the catheter 102 includes a tip 110 with a cooling surface 122 that contacts and cools the tissue to be treated. The device 100 includes mechanisms to manipulate the curvature of the deflectable segment 107, and may also include mechanisms to retain a set curvature using a braking or locking mechanism. Structures in the catheter 102 may be used to oppose the axial tension imparted by the deflection mechanism, to prevent snaking of catheter 102 when a tension is applied by the operator. The catheter 102 may include a mechanism to urge the deflectable segment 107 in a straight position when deflection forces are not applied, so that the catheter 102 remains in a neutral position unless the operator manipulates the deflection mechanism. In one exemplary embodiment according to the present invention, the conduits carrying refrigerant to and from the tip 110 are disassociated from the deflection control mechanism, to reduce the need to hermetically seal the handle 104.

The exemplary embodiment of the cryoablation catheter 102 according to the present invention achieves a large bending angle of the catheter 102, which may exceed 180 degrees, over a very small bending radius. This configuration allows catheter 102 to bend backwards over itself, and reach tissue targets in the patient's body that cannot be reached with conventional devices. The exemplary device also has a tip 110 that provides a large surface area for heat transfer, so that a large surface of tissue may be treated in one application of the tip 110. The large diameter of the tip 110 also provides a large expansion chamber 124 in which the pressurized refrigerant can expand and produce very low temperatures.

The large diameter of catheter 102 in regions adjacent to the deflectable segment 107 allows for effective transfer of mechanical torque from the proximate handle 104 of the device 100 to the tip 110, and also minimizes the pressure drop of refrigerant fluid moving within catheter 102. In the exemplary embodiment shown in FIGS. 1 and 2, the distal tip 110 is a spherically closed hollow tube that may be cast, machined formed or molded from a material that is highly temperature conductive. In one exemplary embodiment, the material may be copper, and may be coated with a biocompatible material such as gold.

A tip union 128 may be used to connect tip 110 to the rest of device 100. Tip union 128 may be made, for example, of a weldable metal, preferably stainless steel. The tip 110 and tip union 128 are attached and hermetically sealed together, for example by soldering or brazing. A hole or slot 130 may be formed on the lateral wall of tip union 128 to permit passage of sensor wires. For example, electrical wires 132 may exit opening 130, or may extend into chamber 124 of tip 110. In one exemplary embodiment, two of the wires 132 may form a thermocouple of copper and constantan wires, to measure the temperature of cooling surface 122. Another one of wires 132 may extend in tip 110 to measure physiological parameters, and may be, for example, made of nickel. All or some of the wires may be coated with an insulating material, such as polyimide or polyamide.

A capillary tube 120 may extend through the length of catheter 102, and may terminate with orifice 136 in chamber 124 of tip 110. In one embodiment, the capillary tube 120 has inner and outer diameters that are significantly smaller than the diameter of catheter 102. Orifice 136 is disposed axially, and at a distance from the inner surface of cooling surface 122 that is selected to allow unrestricted expansion of refrigerant fluid in chamber 124. Capillary tube 120 extends proximally towards handle 104, and may become or may be attached to a high pressure refrigerant line connectable to the refrigeration unit through connector 105. The distal portion of capillary tube 120, orifice 136 and expansion chamber 124 form a liquid/gas phase change expander, capable of cooling surface 122 to a cryogenic temperature.

Figure 2:
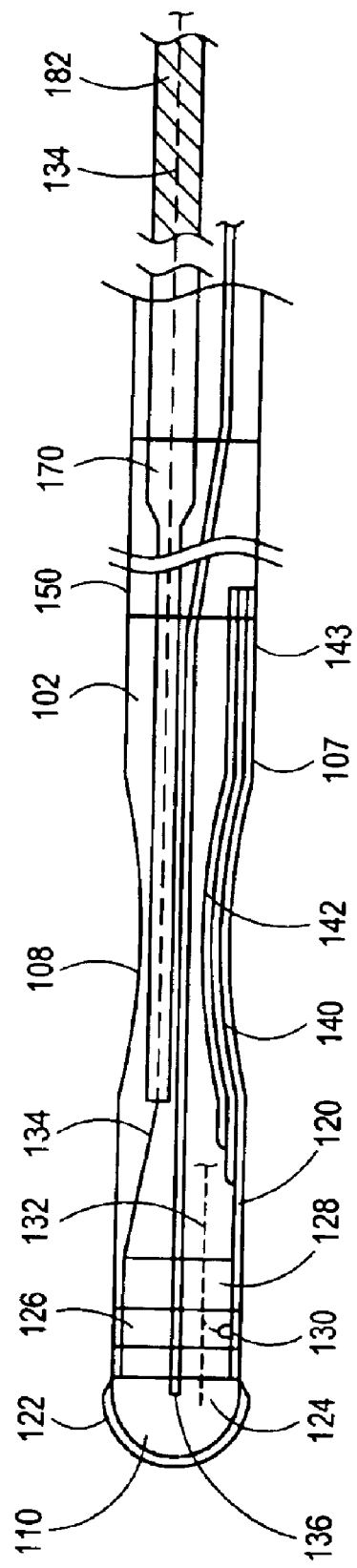
FIG. 2 is a schematic cross sectional view showing a tip portion of the catheter according to an embodiment of the present invention.

In one embodiment, resilient component 140 is attached to an inside portion of catheter 102. Resilient component 140 may be assembled from a plurality of substantially flat metal wires 142, that have a rectangular cross section. Wires 142 may have a mass moment of inertia in one plane that is significantly higher than in other perpendicular planes. For example, the mass moment of inertia of wires 142 may be such that bending within the plane of FIG. 2 is substantially unrestricted, but bending in the perpendicular planes is significantly resisted. In one exemplary embodiment, resilient component 140 extends proximally from near tip union 128 through deflectable segment 107.

In one embodiment, wires 142 are not of equal length, and form a leaf spring having a base flat wire 143 slightly longer than the other wires. Additional flat wires have substantially identical cross sections, and may be stacked on the base flat wire 143 at the proximal end of resilient component 140. The additional wires 142 have progressively shorter lengths, as shown in FIG. 2. In one exemplary embodiment, each of the successive flat wires 142 terminates approximately 1.5 cm before the end of the flat wire immediately below, giving the distal end of resilient component 140 a stepped shape. The base wire 143 in this exemplary embodiment may be approximately 7 cm in length. The successive wires 142 may be selected to give a progressively increasing moment of inertia from the distal to the proximal end of resilient component 140, along the longitudinal direction.

In the exemplary embodiment shown in FIGS. 1 and 2, the distal end of resilient component 140 may be attached by welding or bonding to the tip union 128. The proximal end may be welded or bonded to a shaft union 150 that is disposed at the proximal end of deflectable segment 107. The resulting resilient component 140 has a substantially rectangular cross section, and acts as a spine through the flexible deflectable segment 107. In this manner the bending of deflectable segment 107 is not restricted in a selected plane, but is restricted in every other plane.

Opposite to the resilient component 140, the exemplary embodiment shown in FIG. 2 has a pull wire 134 that can apply a tension to the deflectable segment 107. Pull wire 134 may be attached, for example, to the tip union 128 at a location diametrically opposite to the resilient component 140. Pull wire 134 may extend from tip union 128 to a tensioning mechanism controlled by lever 23 in handle 104, to allow an operator to remotely deflect tip 110. When a tension is applied to pull wire 134, a moment is effected on the flexible deflectable segment 107, causing deflection of the segment 107. When the tension is relieved, a restoring force applied by resilient component 140 tends to straighten catheter 102 to its neutral shape. A lock 24 of conventional design may be used to immobilize lever 23, and retain tip 110 in a selected deflected position.

Pull wire 134 may be attached to tip union 128 at a first circumferential position within catheter 102. Resilient component 140 may be attached to the inner surface of catheter 102 at a second circumferential position that is diametrically opposite to the first position. This configuration ensures that the bending force exerted by pull wire 134 is in the bending plane that is not restricted by the action of resilient component 140.

An exemplary embodiment of the present invention may include a tubular compression spring that is designed to prevent compression of catheter 102, while at the same time allowing its bending. As shown in FIGS. 3 and 4, a spring 160 may be firmly attached to tip union 128 on the distal end, and to shaft union 150 on a proximal end. For example, spring 160 may be attached by bonding, welding or soldering. In one exemplary embodiment, the spring 160 is formed of a flat tubular wire of rectangular cross section, having the narrower of the cross section rectangular dimensions directed radially from the center of the tubular shape, and the wider of the rectangular dimensions directed axially along the tubular spring 160. In the embodiment shown in the drawings, the pitch of the spring 160 may be selected to control bending in planes perpendicular to the catheter axis.

In one exemplary embodiment, the spring 160 is formed of a proximal portion 162 having a higher pitch, meaning smaller gaps between the coils, and a distal portion 164 having a lower pitch. This configuration helps control bending of the catheter 102 in the desired plane, with a desired resistance to bending, since the coils of spring 160 act as ribs in deflectable segment 107. In an exemplary embodiment, the outer diameter of springs 160 may be smaller than the diameter of tip 110, depending on the desired bending radius of catheter 102.

A shaft union 150 may be located adjacent to spring 160. In one exemplary embodiment, the shaft union 150 is formed of a thin walled cylindrical member, having a wall thickness of less than approximately 0.003 in. The shaft union 150 may be welded or brazed to the proximal end of compression spring 160. A sheath union 170, shown in FIG. 2, may be formed from a single lumen metal tube having an inner diameter at one end smaller than the inner diameter at the opposite end, with a stepped diameter in between. The end of sheath union 170 with the smaller diameter may be inserted into and fixed to an inner edge of shaft union 150, while the opposite end extends proximally from the shaft union 150.

The various structures contained within deflectable segment 107, such as compression spring 160, resilient component 140 and pull wire 134, do not interfere with the shape of reduced diameter section 108. As described above, the minimum diameter of reduced diameter section 108 is smaller than the diameter of the rest of catheter 102, specifically it is smaller than the diameter of tip 110 and of shaft union 150. The precise location of the minimum diameter can be optimized depending on the required performance of device 100, but will preferably be located between tip union 128 and shaft union 150.

In the embodiment according to the invention shown in FIG. 2, pull wire 134 extends from the tip union 128 towards the proximal end of catheter 102, and passes through the lumen of sheath union 170 and through the passage defined by compression spring 160. The rectangular spine formed by resilient component 140 also extends into the shaft union 150, and may be firmly attached thereto. Sensor wires within wires 132 pass through compression spring 160 and then shaft union 150 before extending proximally towards the handle 104. Capillary tube 120 that carries high pressure refrigerant also passes through shaft union 150, while the low pressure refrigerant returning to the refrigeration unit may pass through the central lumen of compression spring 160, or any other area inside catheter 102 that is not taken up by other components.

A sensor band 126 may be included near the tip 110 of catheter 102. Sensor band 126 may be made, for example, of platinum or other biologically inert material, and may be fused about a formed or molded polymer collar. In one exemplary embodiment, the polymer may be Pebax, and sensor band 126 may be mounted approximately 2 mm from tip 110. Sensor band 126 may be connected to one of wires 132 that passes through opening 130 in tip union 128 and may be used for example to sense ECG electrical impulses.

A flexible jacket may be used to cover all the principal elements of catheter 102 in one exemplary embodiment of the invention. As shown in FIGS. 3 and 4, flexible jacket 180 may extend from the tip union 128 to shaft union 150. A combination of thermal fusion and adhesive bonding may be used to attach the jacket 180. Flexible jacket 180 may be a tube extruded from an elastomeric polymer, and may have a durometer and a modulus of elasticity that allows the material to bend significantly without incurring permanent deformations or cold flow. Jacket 180 preferably may have sufficient wall thickness to maintain a circular cross section while bending, without buckling. For example, jacket 180 could resist buckling while bending 180 degrees around a one half inch bending radius. In one embodiment, the jacket 180 has a length of about 5 cm.

In one exemplary embodiment of the assembly process for the cryoablation device 100, jacket 180 initially has a diameter sufficient to easily pass over all elements of the catheter 102. Jacket 180 is then thermally shrunk and fused over the tip union 128, shaft union 150 and compression spring 160. Jacket 180 also follows the shape of reduced diameter section 108, maintaining the shape of that necked region. The combination of jacket 180 over compression spring 160 forms a composite structure that resists buckling during bending, but does not restrict bending excessively. The necking of the reduced diameter section 108 permits bending over a very tight bending radius. An hermetically sealed cavity extending from the tip union 128 to the shaft union 150 is formed by bonding and fusing the jacket 180 in place, facilitating the circulation of refrigerant fluids.

A wire coil sheath 182 may be used to encase the pull wire 134, at least through a portion of its length. In one exemplary embodiment, coil sheath 182 may terminate at its distal end within the proximal side of sheath union 170, and may extend proximally towards handle 104. In one embodiment, coil sheath 182 may be made from tightly wound 0.006 in. wire, and may have an outer diameter of approximately 0.025 in. During activation or deflection of the tip 110, the wire coils of coil sheath 182 oppose the compression force due to the tension imparted on pull wire 134, and prevent the force from being transmitted to other structures of catheter 102. When a compressive force is applied, the coils of coil sheath 182 are packed together, and act as a rigid body to oppose the force.

Embodiments of the cryosurgery device 100 may also include a main catheter shaft 190, which is formed from a long tubular element having an outer diameter greater than the diameter of the flexible jacket 180, and an inner diameter comparable to the outer diameter of shaft union 150. In one embodiment, the shaft 190 is a composite structure able to transmit a torque to the tip 110 during manipulation of catheter 102. For example, the shaft 190 may include a thin walled but relatively stiff inner tube of thermoplastic material with a metallic wire braid placed over the inner tube. A more flexible polymer coating may cover the metal braid. In one embodiment, the inner tube may have a thickness of approximately 0.0015 in. to 0.0020 in., the braid may be woven from 0.001 in. metal wire and the outer layer may have a thickness of approximately 0.01 in. to 0.015 in. The shaft 190 terminates at its distal end with the shaft union 150, and at its proximal end terminates near handle 104.

In a different exemplary embodiment, the shaft 190 may be made of a thermoplastic extrusion with an embedded stainless steel braid. The material properties of the polymeric extrusion and the pitch and number of wires of the braid are selected to obtain the desired properties of the shaft 190. In one exemplary embodiment of the present invention, a gauge tube 200 extends through the shaft 190. Gauge tube 200 may be a small diameter tube used to monitor the pressure of the return refrigerant fluid from tip 110. For example, the gauge tube 200 may have an outer diameter of approximately 0.029 in. and an inner diameter of approximately 0.024 in.

A sheath tube may also be employed about the wire coil sheath 182, having an inner diameter of, for example, approximately 0.024 in., thus allowing free movement of the wire coil sheath 182 within the tube. The length of the sheath and of the tube are selected so that, during catheter usage, the pressure at the distal end of the sheath tube is below atmospheric pressure. The sheath tube terminates for example within handle 104, where the pressure is atmospheric, and the length and dimensions of the sheath tube are such as to provide a high resistance pathway to fluid movement between catheter 102 and handle 104. According to this embodiment of the invention, the pull wire 134 and the sheath pass through the wire coil sheath 182 so that there is little available space for fluid movement within wire coil sheath 182. Use of this exemplary embodiment permits the sheath and pull wire 134 to exit the interior of catheter 102, which is filled with refrigerant fluid, without leaking taking place. This configuration is advantageous, because it relieves the need to hermetically seal handle 104.

Figure 5A:
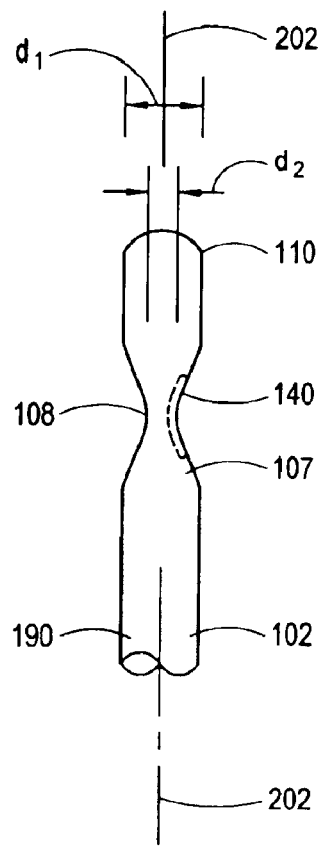
FIG. 5A is a plan view of the distal portion of the cryocatheter shown in its first configuration, with selected internal components shown in phantom for clarity.
Figure 5B:
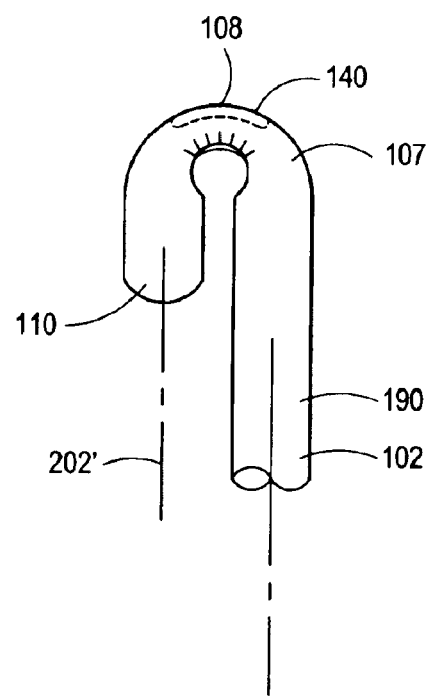
FIG. 5B is a plan view of the distal portion of the cryocatheter shown in its second configuration, with selected internal components shown in phantom for clarity.

In the operation of the device 100 of the present invention, the catheter 102 is inserted into the vasculature of a patient by means well known in the pertinent art. The catheter 102 is then advanced through the vasculature by manipulating the actuating lever 23 to bend the distal tip 110 of the catheter 102 as needed. Specifically, during this manipulation, the distal tip 110 can be deflected to assume shapes between a first configuration (see FIG. 5A) and a second configuration (see FIG. 5B). More specifically, in its first configuration, the distal tip 110 and the main shaft 190 of the catheter 102 are substantially aligned along a common axis 202. On the other hand, in its second configuration, the distal tip 110 defines an axis 202' that is substantially parallel to the axis 202 of the main shaft 190. Thus, as will be appreciated by cross referencing FIG. 5A with FIG. 5B, the deflectable segment 107 can be bent by the actuating lever 23 to deflect the distal tip 110 through an angular range that is approximately equal to 180°.

In the preceding specification, the present invention has been described with reference to specific exemplary embodiments thereof. It will, however, be evident that various modifications and changes may be made thereto without departing from the broadest spirit and scope of the present invention as set forth in the claims that follow. The specification and drawings are accordingly to be regarded in an illustrative rather than restrictive sense.

What is claimed is:

1. A cryogenically cooled apparatus for ablating tissue of a patient, comprising:
   a handle portion;
   an elongated catheter extending distally from the handle, the elongated catheter being adapted to transmit a torque imparted by the handle;
   a main shaft portion of the catheter having a substantially uniform diameter;
   a deflectable segment at the distal end of the main shaft, the deflectable segment having a minimum diameter that is smaller than the diameter of the main shaft;
   a tip portion disposed distally of the deflectable segment and having a diameter greater than the minimum diameter, the tip portion defining an expansion chamber for refrigerant fluid;
   a resilient component adapted to define a preferred plane of deflection of the deflectable segment; and
   an actuator connected to a distal portion of the elongated catheter, adapted to impart a curvature to the deflectable segment.

2. The apparatus according to claim 1, wherein the resilient component is formed by stacked wires having a rectangular cross section, the smallest dimension of the rectangular cross section being in the stacking direction.

3. The apparatus according to claim 2, wherein successive ones of the stacked wires are of decreasing length.

4. The apparatus according to claim 1, further comprising a capillary tube to transport refrigerant fluid from a refrigerant connection adjacent the handle to the tip portion.

5. The apparatus according to claim 2, wherein the stacked wires extend longitudinally along an inner surface of the deflectable segment.

6. The apparatus according to claim 1, wherein the tip portion is made of a heat conductive metal.

7. The apparatus according to claim 1, wherein the actuator is a pull wire linked to the tip portion at a distal end, and attached to a deflection control of the handle at the proximal end.

8. The apparatus according to claim 1, further comprising a tip union connecting the tip portion to the deflectable segment, the tip union having a cylindrical shape, and a shaft union connecting the deflectable segment to a proximal portion of the main shaft.

9. The apparatus according to claim 8, further comprising a compression coil extending between the tip union and the shaft union, the compression coil resisting axial compression.

10. The apparatus according to claim 9, wherein the compression coil has a proximal portion having a higher pitch than the pitch of a distal portion of the compression coil.

11. The apparatus according to claim 1, further comprising a sheath union formed by a hollow cylinder having stepped diameters, the sheath union extending through the shaft union and proximally from the shaft union.

12. The apparatus according to claim 11, further comprising a sheath attached to the sheath union, extending proximally to the handle, the sheath being formed of wire reinforced polymer shell, and being adapted to resist compressive loads.

13. The apparatus according to claim 12, wherein the actuator slidably extends through a lumen of the sheath union and through the sheath.

14. The apparatus according to claim 1, further comprising a sensor band adjacent to the tip, the sensor band being made of a conductive material, and sensor wires connected to the sensor band, extending proximally from the sensor band.

15. The apparatus according to claim 9, further comprising a flexible jacket encasing the compression coil, the flexible jacket being adapted to retain a circular cross section during deflection.

16. The apparatus according to claim 1, wherein the deflectable section has a diameter that varies longitudinally between the diameter of the elongated catheter and the minimum diameter.

17. The apparatus according to claim 16, wherein the deflectable section has a diameter equal to the elongated catheter diameter at a distal end and at a proximal end, and a diameter equal to the minimum diameter between the proximal and distal ends.

18. The apparatus according to claim 1, wherein the main shaft comprises a polymeric inner tube, a metal wire braid surrounding the inner tube, and an outer polymeric encasing the braid.

19. The apparatus according to claim 1, wherein the resilient component is connected to the elongated catheter at a first circumferential position, and the actuator is connected to the elongated catheter at a second circumferential position, diametrically opposite to the first circumferential position.

20. A deflectable catheter for surgical applications, comprising:
a main shaft portion of the catheter having a substantially uniform diameter;
a deflectable segment of the catheter, the deflectable segment having a minimum diameter that is smaller than the diameter of the main shaft;
a tip portion of the catheter disposed distally from the deflectable segment, the tip portion having a diameter greater than the minimum diameter;
a resilient component adapted to define a preferred plane of deflection of the deflectable segment; and
an actuator linked to the tip portion of the catheter, adapted to impart a curvature to the deflectable segment.

21. The catheter according to claim 20, wherein the resilient component is formed by stacked flat wires having a rectangular cross section, the smallest dimension of the rectangular cross section being in the stacking direction.

22. The catheter according to claim 21, wherein a base wire of the flat wires is disposed longitudinally along an inner surface of the deflectable segment, and successive wires are stacked radially on the base wire.

23. The catheter according to claim 20, wherein the actuator is a pull wire linked to the tip portion and extending proximally from the tip portion.

24. The catheter according to claim 20, wherein the actuator is linked to an inner surface of the tip portion at a location diametrically opposite to the resilient component.

25. The catheter according to claim 20, further comprising a compression coil extending along the deflectable section, the compression coil resisting axial compression.

26. A cryocatheter with a deflectable tip for use in surgical applications which comprises:
a main shaft portion having a substantially constant first diameter ($d_1$);
a tip portion having a substantially same first diameter ($d_1$);
a deflectable segment interconnecting said main shaft portion with said tip portion, said deflectable segment having a distal end connected to said tip portion and a proximal end connected to said main shaft portion with a mid point therebetween, said deflectable segment having a second diameter ($d_2$) at the midpoint wherein said second diameter is less than said first diameter ($d_1 > d_2$);
a resilient component mounted in said deflectable segment adapted to define a preferred plane of deflection for said deflectable segment; and
an actuator mounted on said main shaft portion and connected to said tip portion to move said tip portion through a range in the preferred plan of deflection between a first configuration wherein said tip portion is substantially coaxial with said main shaft portion and a second configuration wherein said tip portion is approximately parallel with said main shaft portion.

* * * * *